United States Patent [19]

Aoki et al.

[11] Patent Number: 4,748,156

[45] Date of Patent: May 31, 1988

[54] THROMBIN-BINDING SUBSTANCE AND PROCESS FOR PREPARING THE SAME

[75] Inventors: Nobuo Aoki, Tokyo; Masami Shiratsuchi, Musashimurayama; Shigeru Kimura, Higashiyamato, all of Japan

[73] Assignee: Kowa Co., Ltd., Nagoya, Japan

[21] Appl. No.: 3,465

[22] Filed: Jan. 15, 1987

[30] Foreign Application Priority Data

Jan. 21, 1986 [JP] Japan .................. 61-10620

[51] Int. Cl.$^4$ .......................... C07K 3/20; C07K 3/28
[52] U.S. Cl. ......................................... 514/21; 514/8; 424/85; 424/105; 530/350; 530/413; 530/419; 530/399
[58] Field of Search ............... 530/350, 413, 419, 399; 424/105, 85; 514/8, 21

[56] References Cited

U.S. PATENT DOCUMENTS

| | | | |
|---|---|---|---|
| 4,254,021 | 3/1981 | Bohn et al. | 424/85 X |
| 4,301,064 | 11/1981 | Bohn | 424/85 X |
| 4,302,385 | 11/1981 | Bohn et al. | 424/85 X |
| 4,368,148 | 1/1983 | Bohn | 424/85 X |
| 4,402,872 | 9/1983 | Bohn | 424/85 X |
| 4,468,345 | 8/1984 | Bohn et al. | 530/387 |
| 4,500,451 | 2/1985 | Bohn et al. | 424/85 X |
| 4,507,229 | 3/1985 | Bohn | 424/101 X |
| 4,594,328 | 6/1986 | Bohn et al. | 424/105 X |
| 4,599,318 | 7/1986 | Bohn et al. | 530/419 X |
| 4,638,050 | 1/1987 | Aoki et al. | 530/350 X |

OTHER PUBLICATIONS

J. Biol. Chem. 257(2), 859–864 (1982), Esmon et al.
Thromb. Res. 37, 353–364 (1985), Esmon et al.
J. Clin. Invest. 75, 987–991, (Mar. 1985), Maruyama et al.

*Primary Examiner*—Howard E. Schain
*Attorney, Agent, or Firm*—Oblon, Fisher, Spivak, McClelland & Maier

[57] ABSTRACT

A novel thrombin-binding substance having the characteristics of (a) molecular weight: 47,000±6,000 in reduced condition and 38,000±6,000 in unreduced condition, (b) isoelectric point: pH 4.9–5.7, (c) affinity: strong affinity to thrombin, (d) activity: (1) capable of promoting the thrombin catalyzed activation of protein C, (2) prolongs clotting time; and (e) stability: stable to denaturing agents (urea sodium and dodecylsulfate), can be prepared from a human placenta by means of extraction, fractionation using ion exchange chromatography and affinity chromatography, and/or gel filtration, followed by electrophoresis. The substance is useful as a medicine for the treatment of thrombosis.

6 Claims, 1 Drawing Sheet

THROMBIN-BINDING SUBSTANCE AND PROCESS FOR PREPARING THE SAME

BACKGROUND OF THE INVENTION

1. Field of the Invention

The present invention relates to a novel thrombin-binding substance associated with fibrinolytic or anticoagulation systems. More particularly, this invention relates to a thrombin-binding substance, which is useful as a medicine especially in the treatment of thrombosis, and to a method for the production of this substance.

2. Description of the Prior Art

Extensive work has been devoted to thrombin which plays an important role as a proteolytic enzyme in the mechanism to control clotting (blood coagulation) in the organism, and a great deal of knowledge has been accumulated to clarify the mechanism by which the thrombin operates.

N. L. Esmon et al. have recently reported that thrombin accelerates the activation of protein C which presumably acts on the fibrinolytic and the anticoagulant systems. They reported the presence of a certain substance in extracts of rabbit lung tissue functioning as a coenzyme for such activation mechanism, and named it thrombomodulin (J. Biological chemistry, 257(2)859–864, 1982).

Aoki, one of the inventors, and others also separated human thrombomodulin from human placenta. The substance had similar properties with that reported by N. L. Esmon et al., with a molecular weight of about 71,000 in a unreduced condition (Thromb. Res. 37, 353–364, 1985).

Furthermore, I. Maruyama et al. separated human thrombomodulin from human placenta with a molecular weight of about 75,000, and compared it with the rabbit thrombomodulin stated above to find that both had identical activities (J. Clin, Invest. 75, 987–991, March 1985).

SUMMARY OF THE INVENTION

The present inventors have been working to find an efficient method for isolating and purifying the above human thrombomodulin, and have succeeded in isolating a substance displaying the same activity but having a lower molecular weight than the human thrombomodulin.

The object of this invention is therefore to provide a novel human thrombin-binding substance and a method for the production thereof.

The thrombin-binding substance of this invention is useful as a fibrinolytic accelerator or as an anticoagulant since it binds with thrombin and remarkably enhances the activation of protein C and prolongs the clotting time.

DETAILED DESCRIPTION OF THE INVENTION AND PREFERRED EMBODIMENTS

Figure 1:
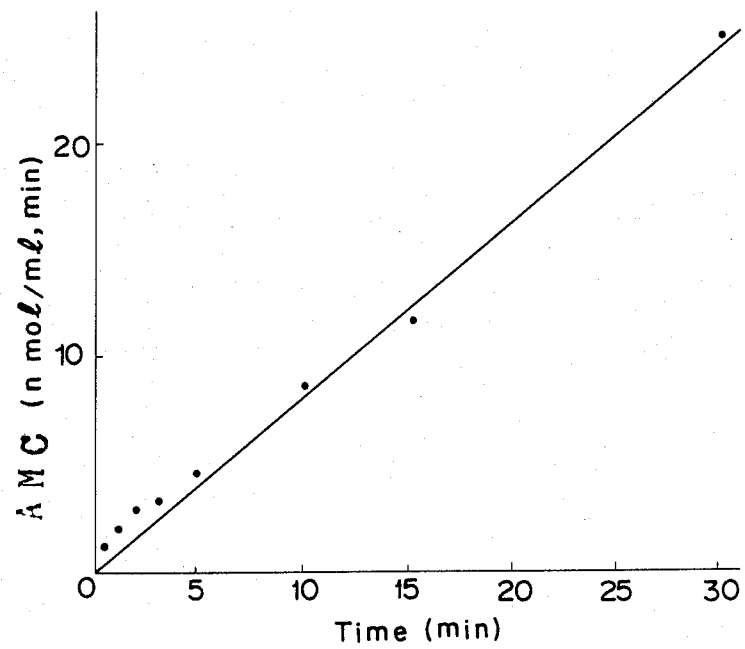
FIGS. 1 and 2 illustrate the accelerating action of the substance of the present invention on the activation of protein C by thrombin.

According to the present invention, the thrombin-binding substance can be prepared by extracting disrupted human placenta with a buffer solution containing a non-ionic surfactant, fractionating the resultant extract by means of ion-exchange chromatography and affinity chromatography using thrombin-bound carrier, and/or gel filtration, and further subjecting the thus obtained fractions to electrophoresis.

Human placenta is first washed with a buffer, for example, a Tris HCl buffer solution containing sucrose and benzamidine HCl, and is disrupted for homogenization. The material thus prepared is then loaded into a centrifuge to collect precipitates which are subsequently extracted with a solution prepared by adding a non-ionic surfactant such as Triton X-100 to the above buffer. The extract is then fed to a column packed with thrombin-bound carrier such as disopropylphosphoro(-DIP)-thrombin-agarose to adsorb active fractions which are subsequently eluted by Tris HCl buffer containing sodium chloride, EDTA, benzamidine HCl and Lubrol PX. Otherwise, the above extract may be treated with the gel filtration method. The gel filtration may be employed alone or in combination with the ion exchange chromatography and the affinity chromatography.

The substance of the present invention can be produced by performing electrophoresis on the active fraction by means of sodium dodecylsulfate (SDS)-polyacrylamide gels and collecting a fraction having the molecular weight of this invention according to, for example, the Laemmili's method as described in Nature, 227, 580–685, 1970.

The thrombin-binding substance thus obtained has the following properties:

(a) Molecular weight
  47,000±6,000 in reduced condition
  38,000±6,000 in unreduced condition
  Measuring method:
  Molecular weights were determined by electrophoresis using 7.5% SDS-polyacrylamide gels containing 5% urea according to Laemmili's method as described in Nature, 227, 680–685, 1970.

The standard protein was Bio-Rad SDS-PAGE standard for high-molecular weighs produced by Nippon Bio-Rad Laboratory Inc. The reducing treatment was carried out with 2% dithiothreitol at 100° C. for three minutes.

(b) Isoelectric point
  pH 4.9–5.7
  Ampholite was used to determine an isoelectric point for each fraction in electrophoresis.

(c) Affinity
  The substance of the present invention has a strong affinity with thrombin. Nearly 100% of the substance of this invention was adsorbed in a chromatographic treatment using DIP-thrombin-agarose as shown in J. Biological Chemistry, 245,3059–3065, 1970.

(d) Activity
  (1) The substance of the present invention combines with thrombin to activate protein C.

Measuring method 1:
  5 μl of 7.2 μM protein C, 0.5 μl of a 0.055A $_{280}$/ml solution of the present invention and 50 μl of 4U/ml -thrombin were dissolved in 40 μl of 0.02M Tris HCl buffer (PH 7.5) containing 0.1M sodium chloride and 3.5 mM calcium chloride. The solution was then incubated at 37° C. for 0–30 minutes. 150 μl of 16.1 μM antithrombin III was added and incubated at 37° C. for 15 minutes, whereupon the reaction was terminated. To this solution, 250 μl of buffer containing 100 μM Boc-Leu-Ser-Thr-Arg-MCA, produced by Protein Research Foundation, Osaka, Japan, was added to react at 37° C. for 10 minutes. Afterwards, 500 μl of 20% acetic acid was added to terminate the reaction. The concentration of the dissociated AMC was measured by fluorescence spectrophotometry with an exciting light wave-length of 380 nm and an emitting light wavelength of 460 nm.

The results are shown in FIG. 1.

Figure 2:
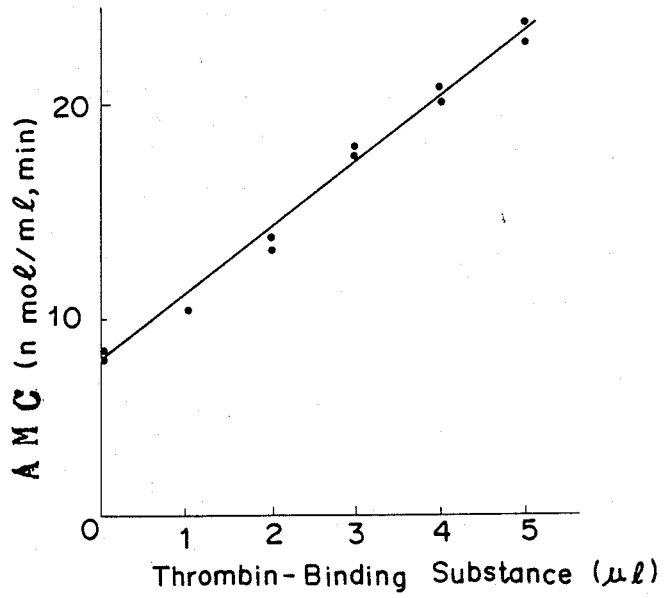

Measuring method 2:

5 μl of 7.32M protein C, 0 -5 μl of a 0.055 $A_{280}$/ml-solution of the present invention, 0–5 μl of 0.02M Tris HCl buffer (pH 7.5) containing 0.1M sodium chloride and 0.5% Lubrol PX produced by Sigma Co., and 50 μl of 4U/ml thrombin were dissolved in 40 μl of 0.02M Tris HCl buffer (pH 7.5) containing 0.1M sodium chloride and 3.5 mM calcium chloride. The solution was then incubated at 37° C. for 30 minutes. 150 μl of antithrombin III was then added and incubated at 37° C. for 15 minutes, whereupon the reaction was terminated. The concentration of the dissociated AMC was measured using the MCA substrate according to the same procedure as described for measuring method 1. The results are shown in FIG. 2.

It can be seen from these results that the substance of this invention indeed accelerates the activation of protein C by thrombin.

(2) The substance of the present invention prolongs blood clotting time.

Measuring method:

100 μl of 1U/ml cow thrombin produced by Mochida Pharm. Co. and 100 μl of the substance of this invention or human thrombomodulin ($A_{280}$:0.42, 0.84) were put into a fibrocup and heated at 37° C. for 30 minutes. 100 μl of 2 mg/ml human fibrinogen was then added to measure the clotting time using a fibrometer manufactured by Becton-Dickinson Co. The measurements were made twice to obtain the results shown in Table 1.

TABLE 1

| Sample Concentration ($A_{280}$) | Clotting Time (sec.) | | | |
|---|---|---|---|---|
| 0 (control) | 35.8 | | 36.3 | |
| | Substance of this invention | | Human thrombomodulin | |
| 0.42 | 62.3 | 61.8 | 44.4 | 44.9 |
| 0.84 | 109.9 | 113.3 | 62.9 | 75.4 |

The results shown above indicate that the clotting time increases with an increase in concentration of the substance of this invention and that the substance of this invention possesses the anticoagulating effect.

In addition, it can be seen from the results that the substance of this invention is as twice active as human thrombomodulin.

(e) Stability

| Conditions | Residual Activity |
|---|---|
| Reduction by 1% β-mercaptoethanol | 0.2 |
| Denaturing agent | |
| 1% SDS | 124 |
| 8 M urea | 90 |
| 6 M guanidium chloride | 80 |
| pH 2 | 70 |
| pH 10 | 80 |
| Pepsin treatment | 58 |
| Chymotrypsin treatment | 24 |

-continued

| Conditions | Residual Activity |
|---|---|
| Trypsin treatment | 80 |

The substances of this invention (0.045$A_{280}$) at 25° C. for 150 minutes under the conditions described above. After being treated, the sample was diluted hundredfold with 0.02M Tris NaCl buffer to measure its activity. The residual activity was calculated and expressed as the percentage of the activity of the non-treated substance. The final concentrations of pepsin, chymotrypsin and tripsin were 2.5 μg/ml (pH 2.5), 2.5 μg/ml (pH 7.5) and 2.5 μg/ml (pH 7.5), respectively and the treatments were all conducted at 37° C. for eight hours.

The present invention will be more clearly understood by referring to the following examples, in which the "unit" as used for expressing the relative activity of the substance of the present invention represents the activity for dissocating 1 n mol/ml of AMC per unit time (min.).

EXAMPLE 1

(1) Approximately 450 g of human placenta was washed with 700 ml of 0.02M Tris HCl buffer (pH 7.5) containing 0.25M sucrose, 1 mM benzamidine-hydrogen chloride, 10U/ml aprotinin, and 2 mM diisopropylfluorophosphate (DFP), and then disrupted for homogenization. The homogenized solution was centrifuged at 30,000×g for 40 minutes to separate the precipitates which were then suspended in the above buffer. The slurry was again fed to the centrifuge to yield precipitates. The cycle of reslurry and centrifugation was repeated five times. The final precipitates were extracted with 1 liter of 0.02M Tris HCl buffer (pH 7.5) containing 0.25M sucrose, 1 mM benzamidine-hydrogen chloride, 10U/ml aprotinin, 2 mM DFP, and 0.5% (v/v) Triton X - 100 produced by Sigma Co.

The optical absorbance and relative activity of the extract thus obtained were $A_{280}$=33.5 and 1.1 units-/$A_{280}$, respectively.

(2) 500 ml of the extract was run on a DEAE-Sephadex column, 2.5 cm×70 cm, which had been allowed to reach an equilibrium with the buffer used for the extraction. Then 1.2 l of the same buffer as described above was used to wash the column.

The column was then eluted by 1 l of 0.02M Tris HCl buffer (pH 7.5) containing 1M sodium chloride, 0.1 mM EDTA, 1 mM benzamidine-hydrogen chloride and 0.5% (v/v) Lubrol PX produced by Sigma Co.

(3) 1 l of the thus obtained eluate was dialysed three times against 0.02M Tris HCl buffer containing 0.1M sodium chloride, 0.1 mM EDTA and 0.5% (v/v) Lubrol PX. the solution thus dialyzed was loaded into a DIP-thrombin-agarose column, 2.5 cm×20 cm, which had been equilibrated with the above buffer, and was washed with 2 l of the buffer.

Then, the column was eluted with linear gradient from 0.1M to 1M sodium chloride in 0.02M Tris HCl buffer (pH 7.5) containing 0.1 mM EDTA, 1 mM benzamidine-hydrogen chloride and 0.5% (v/v) Lubrol PX. The active fractions were collected in the amount of 14 ml for each fraction.

The optical absorbance and relative activity of the active fraction were $A_{280}$=0.294 and 2.14 units/$A_{280}$, respectively.

(4) 100 ml of the active fraction was concentrated to about 5 ml using Millipore CX-10 and then run through an ACA34 column, 2.7 cm×100 cm, manufactured by LKB Co., which had been equilibrated with 0.02M Tris HCl buffer containing 0.1M NaCl, 0.1 mM EDTA, 0.5% (v/v) Lubrol PX and 1 mM benzamidine-hydrogen chloride for elution with the above buffer. The active fractions were collected in the amount of 10 ml for each fraction. The optical absorbance and relative activity of the active fraction were $A_{280}=0.008$ and 540 units/$A_{280}$ respectively.

(5) Using Millipore CX-10, the active fraction thus obtained was concentrated to about 5 ml, to which a solution of 5 ml 20% SDS, 1 ml 0.01% bromo phenol blue and 1 ml 50% glycerol were added, and the mixture was heated at 100° C. for two minutes. Then, the active fraction was separated by electrophoresis using 5% urea-7.5% SDS polyacrylamide gels, according to Laemmli's method as described in Nature, 227, 680-685, 1970. The active fraction was then eluted at 4° C. for 24 hours with 0.02M phosphate buffer (pH 7.5) containing 1% Tween 80 and 0.1M sodium chloride.

The eluate was concentrated to about 5 ml using Millipore CX-10. A protein concentration of 140 μg/ml was obtained by the Bradford method as described in Anal. Biochem. 72, 248, 1976.

EXAMPLE 2

The same procedures as those described in Example 1 were repeated, except that the eluent used at stage (2) was 0.02M Tris HCl, pH 7.5 buffer containing 1M sodium chloride, 0.5% Lubrol PX, 0.1 mM EDTA and 6M urea. The optical absorbance and relative activity of the elute were found to be $A_{280}=5.9$ and 3.1 units/$A_{280}$ respectively.

What we claim is:

1. A thrombin-binding substance derived from human tissue obtained by (1) extracting human tissue with a buffer containing a non-ionic surfactant, (2) isolating said thrombin-binding substance in pure form from the resulting extract by diisopropylphosphorothrombin affinity chromatography, (3) subjecting isolate to SDS-polyacrylamide electrophoresis and (4) elution of said thrombin-binding substance having the following characteristics:
   (a) molecular weight:
      47,000±6,000 in reduced condition
      38,000±6,000 in unreduced condition
   (b) isoelectric point: pH 4.9-5.7
   (c) affinity: strong affinity to thrombin
   (d) activity:
      (1) capable of promoting the thrombin catalyzed activation of protein C
      (2) prolongs clotting time; and
   (e) stability: stable to denaturing agents, urea and sodium dodecylsulfate.

2. A process for preparing a thrombin-binding substance having the following characteristics:
   (a) molecular weight:
      47,000±6,000 in reduced condition
      38,000±6,000 in unreduced condition
   (b) isoelectric point: pH 4.9-5.7
   (c) affinity: strong affinity to thrombin
   (d) activity:
      (1) capable of promoting the thrombin catalyzed activation of protein C
      (2) prolongs clotting time; and
   (e) stability: stable to denaturing agents, urea and sodium dodecylsulfate, which comprises:
      (1) extracting human placental tissue with a buffer solution containing a non-ionic surfactant,
      (2) fractionating said resultant extract by means of affinity chromatography using a thrombin-bound carrier, and
      (3) further subjecting the thus obtained fractions to electrophoresis.

3. The process of claim 2, wherein said affinity chromatography is carried out upon a resin of diisopropylphosphorothrombin.

4. The thrombin-binding substance according to claim 1, wherein said human tissue is human placental tissue.

5. A method of promoting the thrombin catalyzed activation of protein C which comprises the administration of a thrombin-binding substance obtained by (1) extracting human tissue with a buffer containing a non-ionic surfactant, (2) isolating said thrombin-binding substance in pure form from the resulting extract by diisopropylphosphorothrombin affinity chromatography, (3) subjecting isolate to SDS-polyacrylamide electrophoresis and (4) elution of said thrombin-binding substance having the following characteristics:
   (a) molecular weight:
      47,000±6,000 in reduced condition
      38,000±6,000 in unreduced condition
   (b) isoelectric point: pH 4.9-5.7
   (c) affinity: strong affinity to thrombin
   (d) activity: (1) capable of promoting the thrombin catalyzed activation of protein C
      (2) prolongs clotting time; and
   (e) stability: stable to denaturing agents, urea and sodium dodecylsulfate.

6. A method of prolonging the clothing time of blood which comprises the administration of a thrombin-binding substance obtained by (1) extracting human tissue with a buffer containing a non-ionic surfactant, and (2) isolating said thrombin-binding substance in pure form from the resulting extract by diisopropylphosphorothrombin affinity chromatography, (3) subjecting isolate to SDS-polyacrylamide electrophoresis and (4) elution of said thrombin-binding substance having the following characteristics:
   (a) molecular weight:
      47,000±6,000 in reduced condition
      38,000±6,000 in unreduced condition
   (b) isoelectric point: pH 4.9-5.7
   (c) affinity: strong affinity to thrombin
   (d) activity:
      (1) capable of promoting the thrombin catalyzed activation of protein C
      (2) prolongs clotting time; and
   (e) stability: stable to denaturing agents, urea and sodium dodecylsulfate.

* * * * *